United States Patent [19]
Williams

[11] Patent Number: 5,669,391
[45] Date of Patent: Sep. 23, 1997

[54] APPARATUS AND METHOD FOR PRESENTING PATIENT ELECTROCARDIOGRAM AND IMPLANTABLE DEVICE STATUS INFORMATION

[75] Inventor: Michael O. Williams, Sunnyvale, Calif.

[73] Assignee: Ventritex, Inc., Sunnyvale, Calif.

[21] Appl. No.: 667,537

[22] Filed: Jun. 21, 1996

Related U.S. Application Data

[62] Division of Ser. No. 422,022, Apr. 13, 1995, abandoned, which is a continuation of Ser. No. 164,315, Dec. 9, 1993, Pat. No. 5,413,594.

[51] Int. Cl.$^6$ .................................................. A61N 1/37
[52] U.S. Cl. ........................................... 128/697; 607/27
[58] Field of Search .................. 128/697; 364/413.01, 364/413.06; 607/27, 32

[56] References Cited

U.S. PATENT DOCUMENTS

| | | | |
|---|---|---|---|
| 4,223,678 | 9/1980 | Langer et al. | 128/419 |
| 4,295,474 | 10/1981 | Fischell | 128/697 |
| 4,374,382 | 2/1983 | Markowitz | 340/870.01 |
| 4,407,288 | 10/1983 | Langer et al. | 128/419 |
| 4,625,730 | 12/1986 | Fountain et al. | 128/419 |
| 4,757,816 | 7/1988 | Ryan et al. | 128/419 |
| 4,791,936 | 12/1988 | Snell et al. | 128/697 |
| 4,969,465 | 11/1990 | Pless et al. | 128/419 |
| 4,971,058 | 11/1990 | Pless et al. | 128/419 |
| 5,014,701 | 5/1991 | Pless et al. | 128/419 |
| 5,048,521 | 9/1991 | Pless et al. | 128/419 |
| 5,127,404 | 7/1992 | Wyborny et al. | 128/419 |
| 5,217,021 | 6/1993 | Steinhaus et al. | 128/702 |
| 5,285,792 | 2/1994 | Sjoquist et al. | 128/697 |
| 5,313,953 | 5/1994 | Yomtov et al. | 128/696 |

OTHER PUBLICATIONS

"The Marker Channel: Telemetric Diagnostic Aid", Duffin, Jr., *Pace*, vol. 7, Nov.-Dec. 1984, Part II, pp. 1165-1169.

*Primary Examiner*—William E. Kamm
*Attorney, Agent, or Firm*—Steven M. Mitchell; Mark J. Meltzer

[57] ABSTRACT

An implantable cardiac therapy device collects patient ECG and device status information, including cardiac event interval information, why therapy was or was not applied, and patient response to therapy, in connection with an arrhythmic episode and correlates such information in a data frame that may be stored for later telemetric transmission to an external instrument or that may be transmitted in real time to the external instrument. The data frame is decoded and parsed by the external instrument for presentation to an attending physician in a time correlated format.

15 Claims, 5 Drawing Sheets

APPARATUS AND METHOD FOR PRESENTING PATIENT ELECTROCARDIOGRAM AND IMPLANTABLE DEVICE STATUS INFORMATION

This is a division of application Ser. No. 08/422,022, filed on Apr. 13, 1995, now abandoned which is a continuation of Ser. No. 08/164,315, filed on Dec. 9, 1993, now U.S. Pat. No. 5,413,594.

BACKGROUND OF THE INVENTION

1. Technical Field

The present invention relates to implantable cardiac devices. More particularly, the present invention relates to the collection, storage, transmission, processing, and presentation of information provided by an implantable cardiac device.

2. Description of the Prior Art

Implantable cardiac devices, such as pacemakers and defibrillators, have evolved into sophisticated data processing systems that continuously monitor a patient's cardiac activity and apply corrective, often life saving, therapy to the patient's heart in response to detected irregularities in such cardiac activity.

In addition to providing cardiac therapy, known devices are capable of providing a limited amount of information relating to device status and activity at the time of detected cardiac arrhythmias for review by an attending physician or other clinical personnel. Such information is usually accessed through the use of telemetric techniques, i.e. through the use of two-way communications between the implanted device and an external instrument for monitoring and programming of the implanted device and displaying telemetered information from the implanted device. During such telemetric communication, the device is interrogated by the external instrument, and status and other information stored by the device is then communicated to the external instrument.

It is known to monitor the operation of a pacemaker and provide electrocardiogram and associated pacemaker diagnostic information. This approach monitors real time cardiac activity such as patient electrocardiogram ('ECG') and pacemaker recent history such as number of paced events, and number of corrective pulses applied by the device. Such device is useful for patient cardiac monitoring, for example in a physician's office or hospital, but unfortunately does not provide insight into cardiac activity and corrective action taken or not taken by the device apart from such real time monitoring. That is, if the sensed or paced events are not observed by the physician during such real time monitoring, it is not possible to determine with a high degree of precision and accuracy what particular therapy the device provided.

In E. Duffin, *The Marker Channel: A telemetric Diagnostic Aid,* PACE, vol. 7, pages 1165–1169 (November-December 1984) an approach to cardiac monitoring is discussed in which a pacemaker is monitored by telemetric techniques at the same time that a patient's ECG is taken. A printout is generated that plots the ECG information obtained with time-correlated pace therapy information. This information is indicated by specifically encoded signals that are output by the pacemaker.

Although plotting pacemaker activity against ECG data is of some use in diagnosing pacemaker failure and/or functionality or for observing cardiac events in real time, the type of information provided is limited to actual cardiac events that are viewed as they are occurring. Thus, such information does not provide any insight into long term cardiac activity and patient response to corrective therapy applied by the device.

It is also known to monitor a patient's ECG to provide a record of the event that triggers the application of corrective action by the device, as well as the specific action taken by the device, and patient response thereto. Such information is stored for later review and analysis, for example by a physician during a patient visit to the physician's office or at a hospital. See, R. Fischell, *Recorder With Patient Alarm and Service Request Systems Suitable for Use With Automatic Implantable Defibrillator,* U.S. Pat. No. 4,295,474 (20 Oct. 1981) in which a defibrillator stores ECG data with regard to cardiac state immediately before and after the triggering cardiac event. The total number of corrective pulses applied by the device and the total number of fibrillation events are also counted. Such stored activity totals may be output from a simple device memory as well as various housekeeping data that are formatted within a data frame that may also include pre- and post-cardiac event patient ECG data.

However, it is not possible to determine accurately or precisely why the device took the action it did. It is therefore not possible to determine if the device is functioning in an optimal manner or if the device is applying the most appropriate therapy for the arrhythmic episode. Nor does the device indicate in useful detail what specific action was or was not taken by the device, e.g. the voltage of the corrective pulse(s) applied. Rather, the device merely stores a summary of device activity, i.e. the number of fibrillation events and number of corrective pulses applied. Thus, it is difficult for a physician to determine if the therapy should be modified, or if the therapy is being properly applied, e.g. if therapy is not being erroneously applied in response to detection of bigeminal rhythm, or if the voltage of the shock administered by the device is excessive.

Similar devices are also discussed in A. Langer, M. Mower, *Arrhythmia Recorder For Use With An Implantable Defibrillator,* U.S. Pat. No. 4,223,678 (23 Sep. 1980) which provides a defibrillator that may be operated to send ECG and other information to a separate remote recording device by means of telemetric communication; and in G. Fountain, D. Lee, D. Kitchin, *Patient ECG Recording Control For An Automatic Implantable Defibrillator,* U.S. Pat. No. 4,625,730 (2 Dec. 1986) where an alarm signal is generated upon detection of a triggering cardiac event and corresponding defibrillator operation. The alarm alerts the patient who may then operate a recording device and thereby store ECG information that is generated during the cardiac episode for later review by a physician.

The Cadence V100 implantable defibrillator manufactured by Ventritex, Inc. provides both stored and real-time ECGs. It also separately provides diagnostic information regarding the type of arrhythmia detected and responsive therapy applied by the device. The system does not, however, provide a time correlated output of the ECG and device diagnostics which would greatly improve the ability of a physician to analyze device operation and effectiveness.

In another group of state of the art devices, a marker channel is provided with real time ECGs. This channel provides coded markers which are indicative of device operation such as delivery of pacing pulses, sensing of VT, sensing of VF and defibrillation output pulse. While this is helpful information, it does not provide a clear indication of why a particular therapy was or was not applied. Additionally, various false triggering events and/or the successful avoidance of such events is not reported. For example, such devices are not capable of reporting the occurrence of bigeminal rhythm and its appropriate non-treatment.

Given the critical need to continually monitor the heart activity of a patient having a cardiac condition, particularly a patient who requires regular application of corrective heart stimulation, for example a patient who needs an implanted cardiac therapy device, and further, given the need to supervise the actual corrective therapy applied by the device to the patient's heart in response to detected triggering cardiac events, it would be useful to relate cardiac activity with device action throughout each arrhythmic episode, including precise information relating to patient ECG prior to the onset of the arrhythmic episode, the exact therapy applied by the device and the reason why therapy was or was not applied by the device, and the patient's response to such therapy.

It would therefore be an extremely valuable diagnostic measure to provide an actual, rather than approximate or abstract, record of each arrhythmic episode, including pre-episode activity, the arrhythmia diagnosis, therapy applied, and patient response to such therapy. It is also of critical importance that such information be presented in a format that is readily understood by an attending physician, without having the physician waste time in interpreting various unrelated abstracted data to try to approximate the meaning of the complex interplay of several interrelated actions during an arrhythmic episode.

SUMMARY OF THE INVENTION

The present invention provides a method and apparatus for supervising corrective action supplied by an implantable cardiac stimulation device, such as a pacemaker or defibrillator. The invention includes a memory that stores arrhythmic episode information, including patient ECG, device state information, device response and therapy applied, for example why such therapy was applied, and patient response to such therapy.

When the device is interrogated, cardiac episode information is presented to a physician in a format that immediately provides the physician with a readily understood view of the patient's condition before, during, and after the arrhythmic episode, the device's interpretation of related cardiac activity, the actual therapy applied or withheld based upon various corrective strategies programmed into the device, and patient response to such therapy. In this way, the apparatus of the invention acts as a virtual paramedic, able to report to the physician what action it took and why it took that action.

In the preferred embodiment of the invention, an implanted pulse generator receives ECG information from the patient's heart. Patient ECG information is digitized and multiplexed or interleaved with status information, that includes information relevant to therapy delivered by the pulse generator, cardiac episodes diagnosed, etc. The status information is interleaved within sequential refractory periods of the ECG. A resulting data frame may then either be stored in memory by the pulse generator for later telemetric transmission to an external instrument, or the data frame may be immediately transmitted to the external instrument for real time display. When the data frame is received at the external instrument it is decoded and parsed for presentation to a physician. The physician is thus provided with an unambiguous and readily understood display of pulse generator activity, including the specific therapy applied and the reasons why such therapy was deemed the appropriate corrective action to be taken by the device.

DETAILED DESCRIPTION OF THE INVENTION

The invention follows a metaphor for expert system diagnosis of detected cardiac arrhythmias and the application of a most appropriate remedial strategy, based upon state of the art implantable cardiac devices. The invention is intended to be applied to cardiac devices, for example those devices that provide alternative programmed therapy based upon the nature of the detected arrhythmia, the therapy applied, etc.

The invention gathers, formats, and, upon interrogation, presents patient ECG information correlated with device status information along a temporal continuum. For examples of various implantable cardiac devices with which the invention finds ready application reference should be had to the following documents: B. Pless, P. Ball, E. Fain, R. Luceri, *Cardiac Therapy Method With Duration Timer*, U.S. Pat. No. 4,971,058 (20 Nov. 1990), B. Pless, M. Sweeney, R. Winkle, A. Nathan, *Method For Combined Cardiac Pacing and Defibrillation*, U.S. Pat. No. 5,048,521 (17 Sep. 1991), B. Pless, P. Ball, E. Fain, *Cardiac Therapy Method*, U.S. Pat. No. 4,969,465 (13 Nov. 1990), and B. Pless, K. Carroll, *Implantable Cardiac Defibrillator Employing A Digital Waveform Analyzer System*, U.S. Pat. No. 5,014,701 (14 May 1991).

The invention is well suited for use with expert system implantable devices of the type that may be programmed to sense and analyze various cardiac arrhythmias and supply the most appropriate therapy in response to such arrhythmias based upon various programmed therapy strategies. Upon interrogating the pulse generator, a meaningful report is provided to the physician, allowing the physician to continue, alter, or discontinue prescribed therapy as is appropriate. By providing such presentation of patient ECG and related status information, a physician is virtually present for each arrhythmic episode, even after the fact, and may thereby apply insights derived from such presentation, along with judgment and experience, to the treatment prescribed for the patient and thereby improve or adapt such treatment as necessary.

Figure 1:
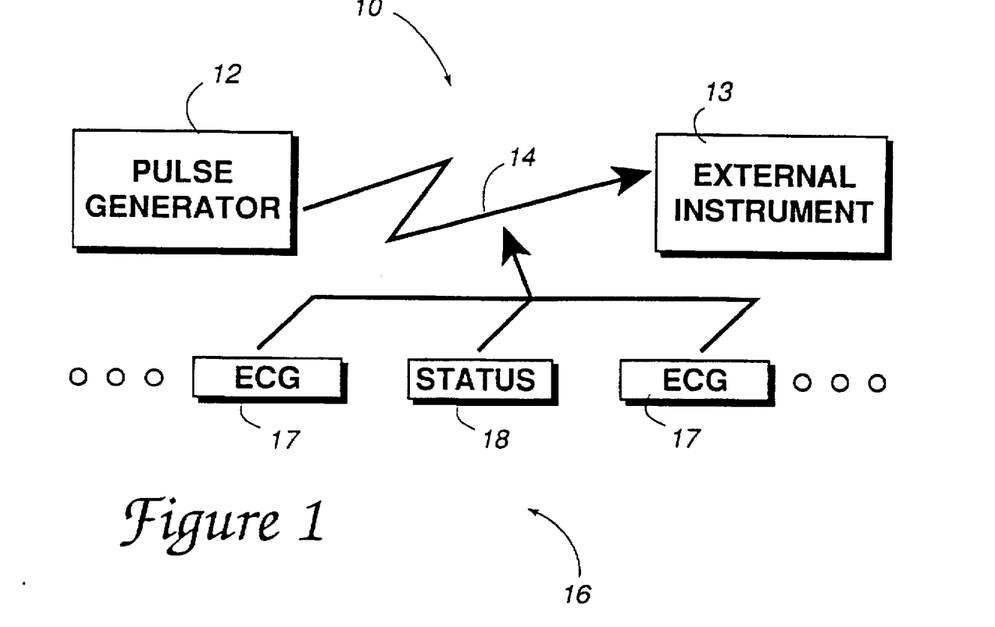
FIG. 1 is a block level schematic diagram of an implantable cardiac device and external instrument according to the present invention.

FIG. 1 provides a block level schematic diagram of a cardiac therapy system 10 including an implantable cardiac device, which is in the preferred embodiment of the invention a pulse generator 12, and external instrument 13, both of which are arranged for telemetric communication of a data frame 16 over a telemetry channel 14. The external instrument 13 programs and interrogates the implanted pulse generator 12, interprets the telemetered data and displays the results. Alternatively, the external instrument function could be performed by several connected instruments. Telemetry is accomplished in the preferred embodiment of the present invention with the use of known telemetry techniques, such as the use of an inductive wand (not shown) which couples information from the pulse generator 12 to the external instrument 13 when the wand is placed over the patient's chest proximate to the pulse generator. Data transmission is initiated when the pulse generator is interrogated by the external instrument, preferably by external instrument transmission to the pulse generator of an enabling code or series of codes.

The data frame 16 (also discussed below in connection with FIG. 4) includes digital information containing patient ECG 17 and device status information 18. Patient ECG and device status information are interleaved within the refractory period portion of the data frame 16 referred to as the status channel. The external instrument receives interleaved patient ECG and device status information in the status channel provided during the refractory period portion of the ECG for each data frame transmitted by the pulse generator, although other data frame formats may also be employed, for example parallel channels, etc. The status information provided by the pulse generator is discussed in greater detail below.

It is important to note that the invention uses the pulse generator to collect patient ECG and device status information and places such information in the data frame in a way that correlates patient ECG to the status information. This is preferably done by placing the immediately current device status information in the data frame during each refractory period. However, the status information can be collected in temporary storage and multiplexed in a time shifted manner with a later occurring refractory period, as long as the particular scheme used is known by the external instrument. Thus, upon receipt of the data frame, the invention employs the external instrument to decode and parse the information in the data frame and present a display that places patient ECG and device status information along a common time line in a readily comprehended format and in a manner that retains temporal consistency between the patient ECG and the device status information.

Figure 2:
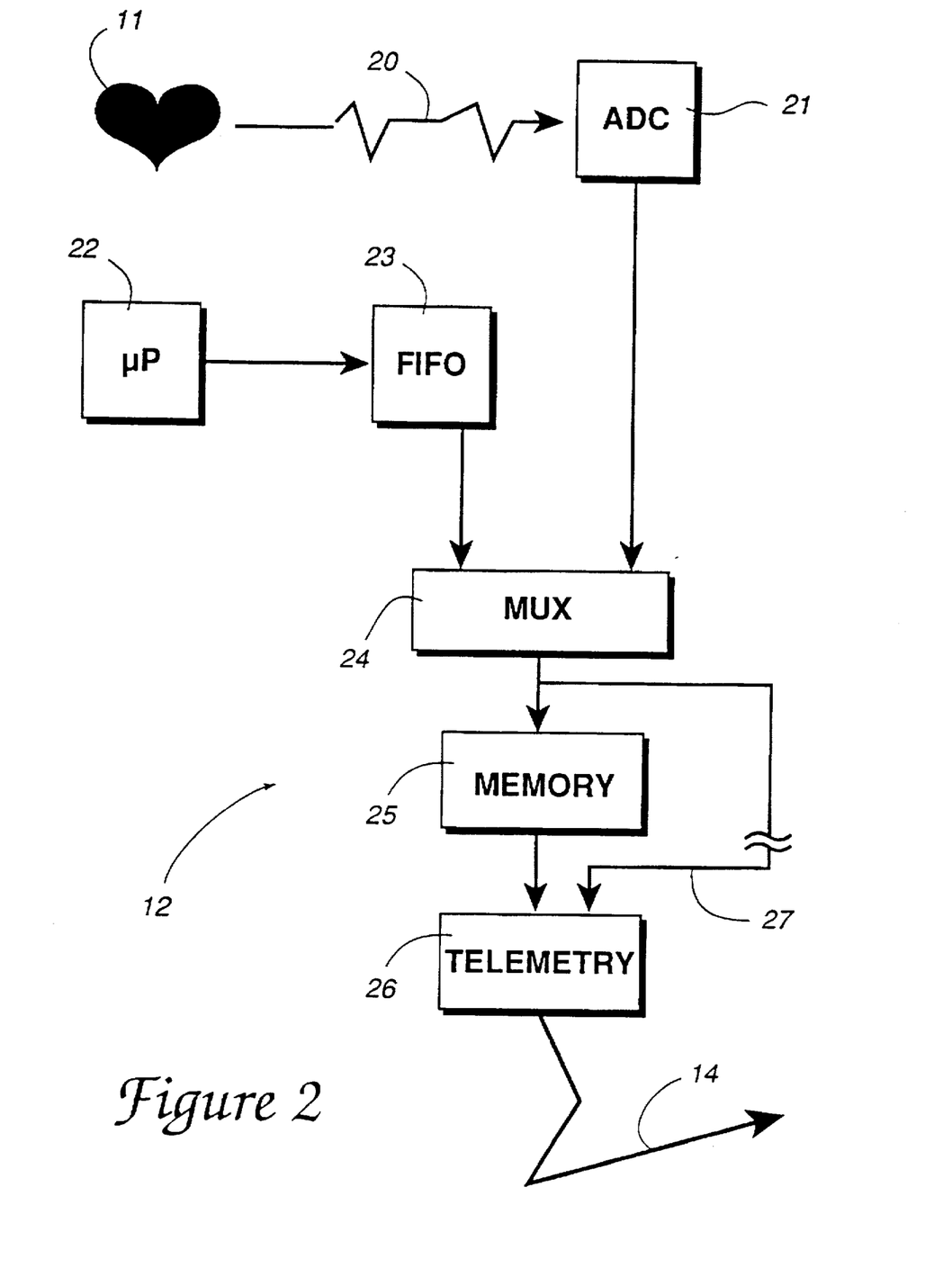
FIG. 2 is a block level schematic diagram of a multiplexing, encoding, and storage circuit for an implantable cardiac therapy device according to the present invention.

FIG. 2 is a block level schematic diagram of an exemplary pulse generator 12. The pulse generator receives patient ECG information from a patient's heart 11 by means of various leads 20 which include sensing electrodes (not shown) and which are implanted in or around the heart by any of the various well known techniques. The information provided by the electrodes through leads 20 is analog. The pulse generator includes an analog to digital converter 21 that converts patient ECG to a digital signal. The digitized patient ECG signal is coupled to a multiplexer, MUX 24.

The multiplexer 24 is also coupled to a FIFO stack 23 which receives device status information for the pulse generator under control of a microprocessor, µP 22. Status information is placed into the FIFO stack in a defined format, such that decoding produces a consistent status report with the information either current or time shifted as discussed above. The various types of status information collected and loaded into the FIFO stack are a function of pulse generator design and types of information required by the attending physician. Thus, the pulse generator may be programmed on a case by case basis to collect that information which is deemed most important. Status information collected and processed in the preferred embodiment of the invention is described in detail below. The preferred embodiment of the invention is implemented in hardware and software using known techniques, but may be implemented completely in hardware in other embodiments of the invention, for example through the use of ASIC's, gate arrays, etc.

The purpose of the multiplexer is to assemble the status channel of the data frame by providing an output that alternately includes, during the refractory period portion of the ECG data stream, digitized patient ECG information and device status information. The remainder of the data frame consists solely of ECG data. The data frame may be stored in a memory 25 for later output by a telemetry means 26, or the data frame may be routed along line 27 to the telemetry means 26 and then directly output to the external instrument.

Figure 3:
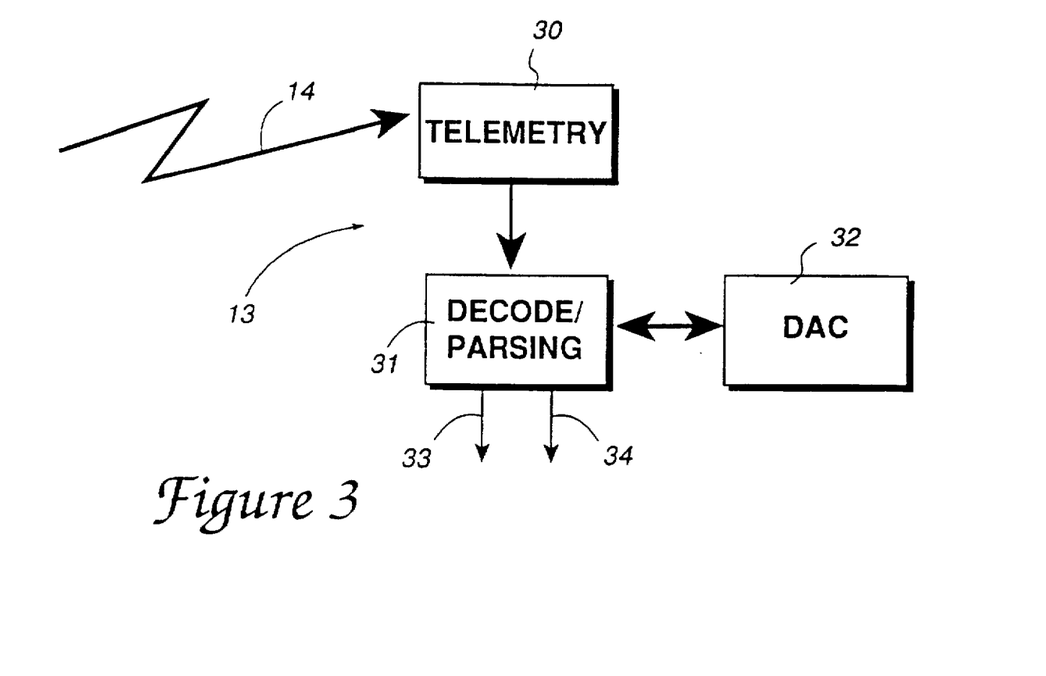
FIG. 3 is a block level schematic diagram of a decoding circuit for an external instrument according to the present invention.

FIG. 3 is a block level schematic diagram of the external instrument 13. Telemetered information 14 is received at an external instrument telemetry means 30 and coupled to a decode and parsing circuit 31. The decode and parsing circuit demultiplexes the patient ECG and device status components of the data frame and routes the patient ECG signal to a digital to analog converter 32 for conversion to an analog ECG signal. The decoded status information is provided along a line 33 to a display (not shown) for presentation along with the analog patient ECG signal, provided along line 34.

Figure 4:
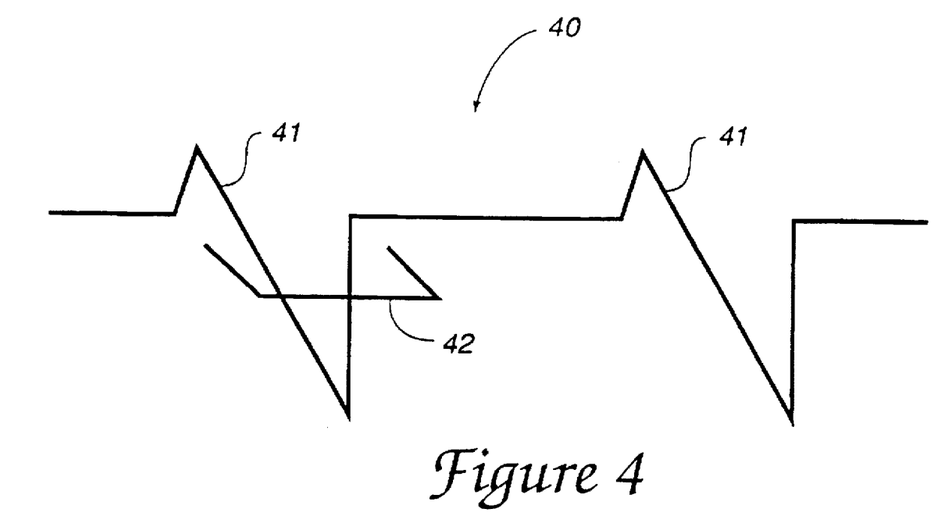
FIG. 4 is a timing diagram showing the presence of a status channel during the refractory period of a paced or sensed complex according to the present invention.

The invention provides a method and apparatus that uniquely relates patient ECG to implantable device status information. FIG. 4 is a timing diagram representing a normal sinus rhythm 40 for a patient's heart. During telemetry, the invention transmits patient ECG and device status information within the status channel portion of the data frame where the portion of the combined data is timed to occur during the refractory period 42 between heart beats 41 in a paced or sensed rhythm.

The invention uniquely takes advantage of the fact that after each heart beat, during an interval referred to as the refractory period (i.e. after the heart cells contract), there is a period of time between 100–500 ms long during which it is not necessary to closely observe heart activity because no significant cardiac events can occur during such interval, i.e. a heart beat has occurred and must be completed before anything can go wrong.

Device status information in the status channel is thus either stored during the refractory period for later transmission or transmitted during the refractory period as part of the real time ECG. Because the interval of the refractory period is Considerable when viewed in terms of electronic devices (on the order of 135 milliseconds or more), the invention is able to store and/or transmit a significant amount of information without losing any important information related to events that occur during such storage and/or transmission. Thus, the preferred embodiment of the invention provides a status channel portion of the data frame of 120 milliseconds during which device status information is interleaved with patient ECG data.

The invention provides various detection rules for detecting arrhythmic episodes, such as distinguishing between pathological tachycardia characterized by sudden onset and sinus tachycardia characterized by gradual onset. The occurrence of these episodes is captured and stored for transmission in the data frame. In this way the invention provides information concerning every action taken or not taken by the pulse generator and the reason why such action was taken or not taken. Status information contained in the status channel portion of the data frame, as well as various diagnostic displays provided by the invention are discussed below.

Status Information included with an ECG

The information defined below for the device status channel exists both in the stored and real-time ECG data streams. The information contained in the status channel is the information needed in conjunction with a stored ECG to fully explain the actions of the device in the preferred embodiment of the invention.

Data supplied for each data frame status channel.

a. Classification of this interval, e.g. non-tach, Tach A, Tach B, fib, deadband, not classified.

b. Reason forstart of charging at this paced/sensed event? E.g. capacitor maintenance, forced charge, charging for device-initiated therapy, charging for commanded therapy.

c. Device state reset occurred sometime before this paced/sensed event?

d. Noise detected at this paced/sensed event?

e. Amplitude of this paced/sensed event, e.g. too high, OK, too low, not classified.

f. Gain setting after this paced/sensed event.

g. Magnet applied, thereby inhibiting the application of therapy at this paced/sensed event?

h. Extended high rate (EHR') had timed out at this paced/sensed event?

i. Temporary modes in effect at this paced/sensed event, e.g. fixed gain, all tach therapies off, none.

j. Bigeminal avoidance satisfied at this paced/sensed event?

k. Sudden onset morphology satisfied at this paced/sensed event?

l. Sudden onset satisfied at this paced/sensed event?

m. AF avoidance morphology satisfied at this paced/sensed event?

n. Atrial fibrillation (AF') avoidance interval irregularity satisfied at this paced/sensed event?

o. Current detected rhythm, e.g. non-tach, Tach A, Tach B, fib, EHR.

p. Commanded shock delivered at this paced/sensed event?

q. Shock aborted at this paced/sensed event?

r. Detection occurred at this paced/sensed event?

s. Diagnosis occurred at this paced/sensed event?

t. Programmer initiated pacing begun at this paced/sensed event?

u. Voltage of therapy delivered at this paced/sensed event?

v. Positive and negative pulse widths of the high voltage shock delivered.

w. Which therapy was delivered, e.g. AT pacing, cardiovert, defib?

x. Interval.

y. Morphology score for this sensed event.

Figure 5:
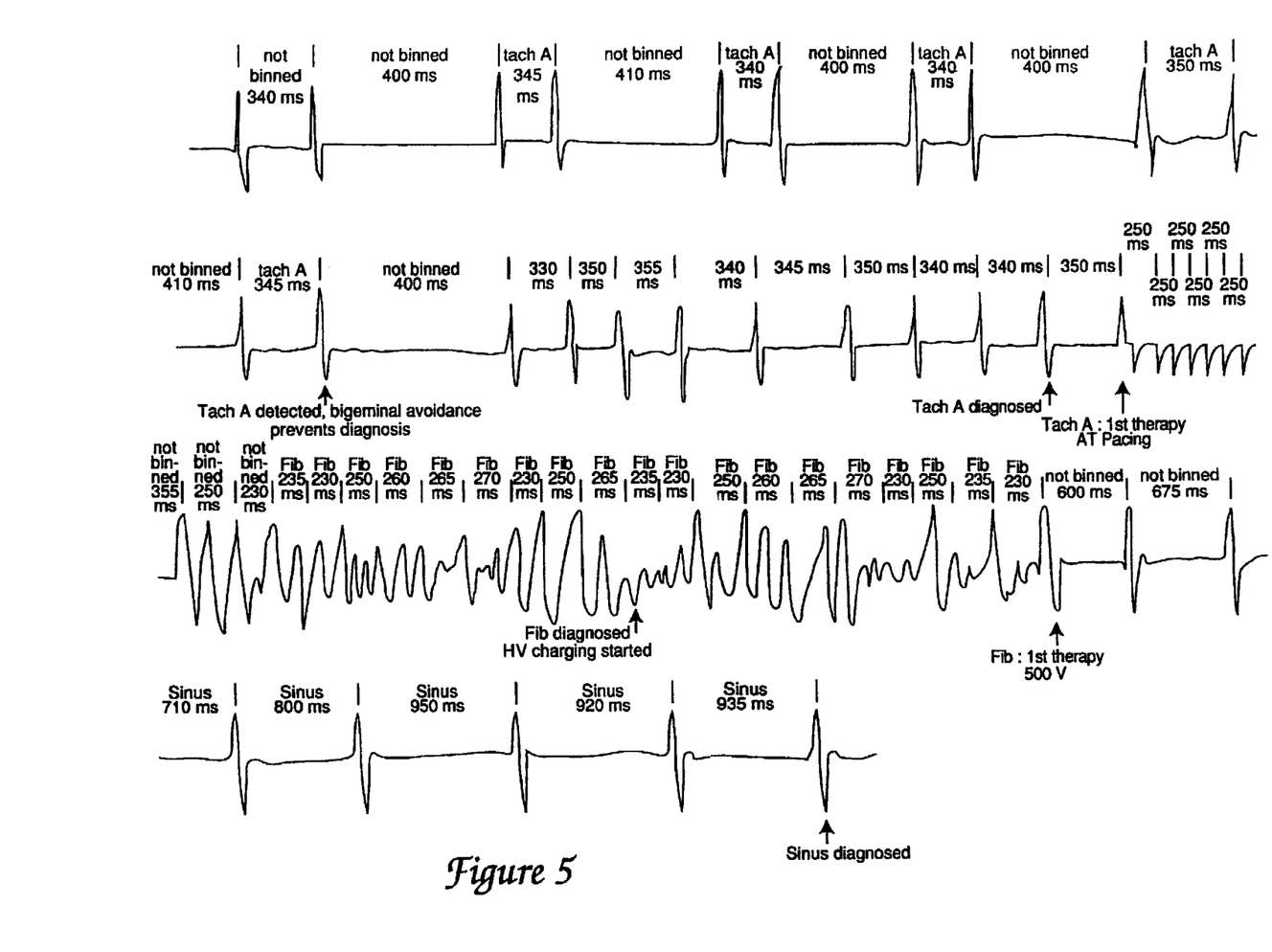
FIG. 5 is an example of a display screen according to the present invention.
Figure 6:
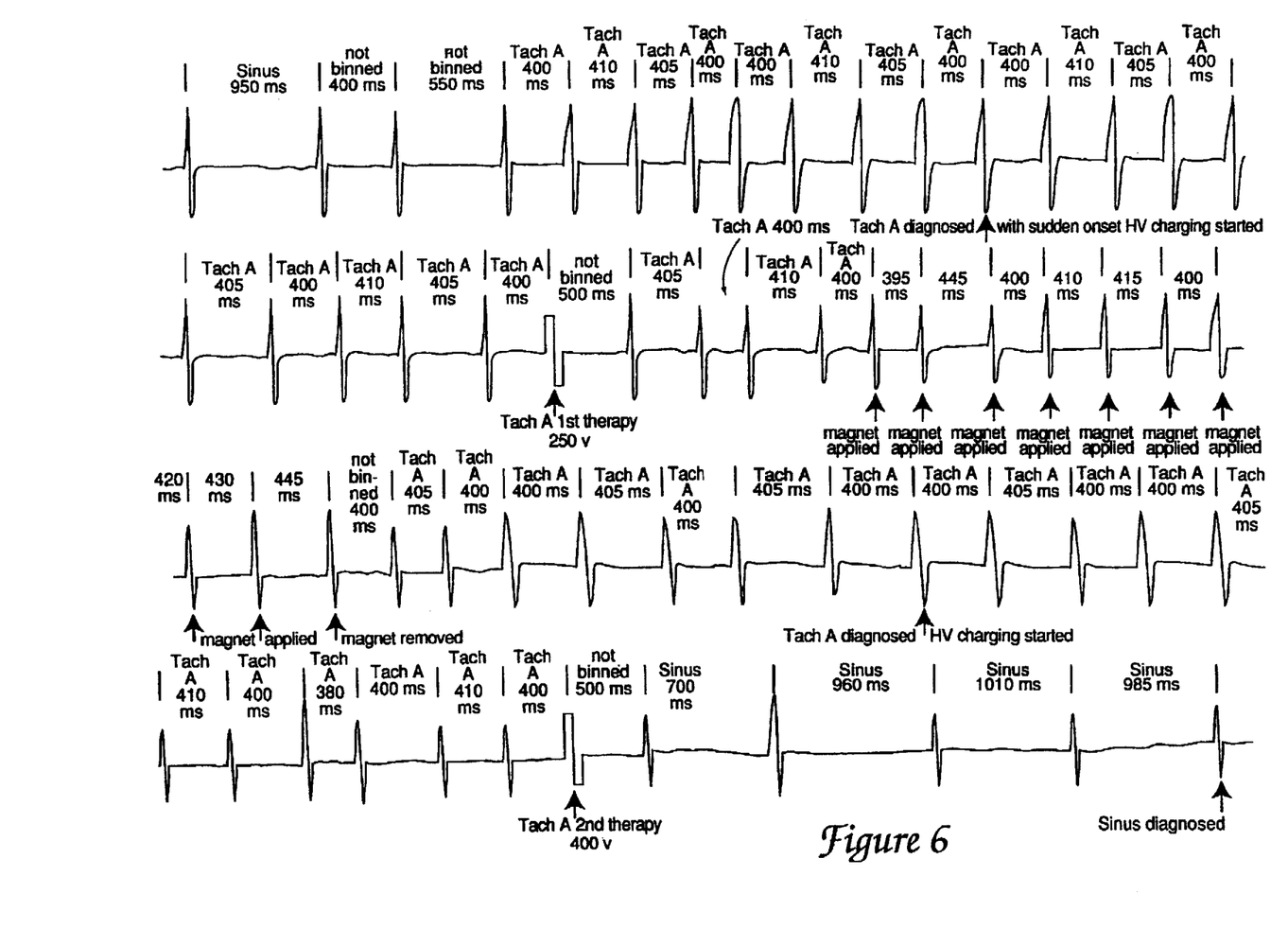
FIG. 6 is another example of a display screen according to the present invention.

FIG. 5 is an example of an information presentation by the invention explaining why the implanted cardiac device did not deliver therapy. Because prior art devices provide simple marker channels that only show what happened, e.g. pacing, start of charge, etc., such prior art devices do not show why an action was taken. Accordingly, such prior art devices also do not explain why an action was not taken. In the following discussion, actual annotations and explanations provided by the device, and which appear in FIGS. 5 and 6, are indicated in the text in parenthesis and quotes ("").

In FIG. 5, the implanted cardiac device is shown to have withheld therapy because a bigeminal rhythm is detected. Beginning at the top of the figure with the first line of the patient ECG it can be seen that a pattern of two close heart beats is detected, followed by a longer interval. This is a bigeminal rhythm and is reported in the presentation as such ("Tach A Detected—Bigeminal Avoidance Prevents Diagnosis"). It is the close spacing of two consecutive heartbeats that gives the appearance of tachycardia.

This pattern repeats, each QRS complex being detected at its peak, as indicated by a vertical line above the R wave. Thus, in the second line of the ECG, it can be seen that at the first rhythm detection, where Tach A is detected, therapy is withheld because a bigeminal rhythm should not be treated by the implanted device.

As the ECG continues, a true tachycardia occurs (on the second ECG line in the figure). Thus, the presentation by the invention indicates why a therapy is to be applied ("Tach A Diagnosed"), and also indicates that the device applied an appropriate therapy ("Tach A 1st Therapy—AT Pacing"). In response to the detected tachycardia, the device applied an antitachycardia pacing therapy.

Beginning at the third line of the ECG, it can be seen that the heart rhythm accelerates to fibrillation, which is diagnosed, and in response to which, the device begins high voltage charging in preparation for administering a corrective shock ("Fib Diagnosed—HV Charging Started"). An interval of time must pass before the device is able to build up a sufficient charge to deliver the programmed therapy. When the device is fully charged, the therapy is administered ("Fib 1st Therapy –500V"). The therapy is successful and the following rhythm is diagnosed as sinus ("Sinus Diagnosed").

Throughout the episode, the information in the status channel is used to display the intervals between cardiac and paced events, the classification of the those intervals, i.e. as Sinus, Tach A, or Fib intervals, and the outcome of the device's rhythm detection. Thus, the presentation provides a summary of all actions taken or not taken and the reason why such actions were or were not taken. This summary is presented in such a way to provide an immediately useful and recognizable representation of an arrhythmic episodes or series of arrhythmic episodes.

FIG. 6 is another example of a presentation of device activity in accordance with the invention. In FIG. 6, the device is prevented from applying therapy due to the presence of a magnet near the device. The use of a magnet to inhibit device operation is generally accepted throughout the industry for such occasions where the device is preferably disabled, such as in a hospital where externally applied therapies are preferred, or during patient examination, where treadmill testing produces an elevated heartbeat that may be incorrectly interpreted by the device as tachycardia.

The figure also shows a rhythm that meets sudden onset criteria programmed into the device. Thus, the sudden change in intervals, having been observed, is treated.

Referring to FIG. 6 in greater detail, it can be seen at the top of the figure in the first line of the ECG that a tachycardia is detected ("Tach A Diagnosed with Sudden Onset—HV Charging Started"). The tachycardia is treated by the device with a 250 volts shock ("Tach A—1st Therapy 250V"). Soon afterward, a magnet is placed near the device to inhibit device operation ("Magnet Applied") which prevents the administration of additional therapy by the device.

Once the magnet is removed ("Magnet Removed"), the device diagnoses a tachycardia rhythm and prepares for the administration of additional therapy ("Tach A Diagnosed—HV Charging Started"). The Tach A therapy is applied ("Tach A—2nd Therapy 400V"), and is successful. The following rhythm is soon diagnosed as sinus ("Sinus Diagnosed").

Throughout the foregoing episode, the status channel of the device provides the intervals between the cardiac and paced events, the classification of those intervals, and the outcome of the device's rhythm detection. All such information is correlated with the patient ECG, such that the ECG is annotated in a manner that shows diagnosis, including qualifying episodes and detected events, as well as therapy delivered, including voltage levels, etc.

Figure 7:
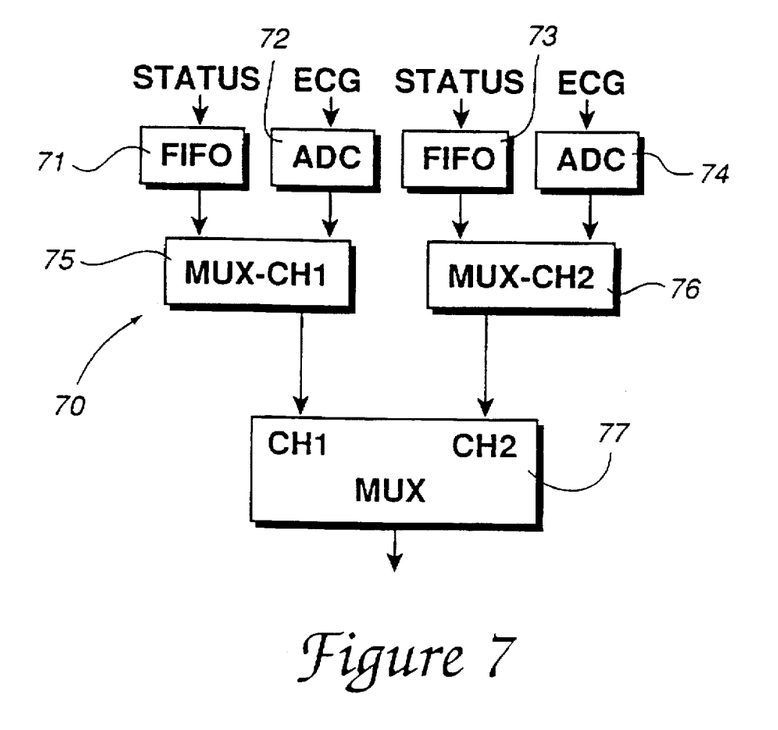
FIG. 7 is a block level schematic diagram of a multichannel circuit for an implantable cardiac device according to another embodiment of the present invention.

FIG. 7 is a block level schematic diagram of a multichannel circuit for an implantable cardiac device according to another embodiment of the present invention. In the figure, device status and patient ECG information are provided on cardiac activity from two locations, e.g. atrial and ventricular activity. Thus, a first channel receives device status information related to a first sensing location at a FIFO 71, and receives patient ECG information at a first ADC 72. This information is multiplexed by a channel 1 multiplexer 75, and is provided as a channel 1 input to a second level multiplexer 77.

A second channel is used to gather data concerning cardiac activity at a second location and provides device status information to a FIFO 73 and provides patient ECG information to an ADC 74. This channel 2 information is applied to a multiplexer 76 and the combined information is then provided to a channel 2 input of the multiplexer 77.

The output of the multiplexer 77 is a two channel data frame that may be stored in a device memory for interrogated telemetry, or that may be immediately telemetered to a remote location (please refer to the discussion above in connection with FIG. 2). This alternate embodiment of the invention is herein described with regard to two channels of cardiac information. However, any number of channels may be provided for use with the invention.

Although the invention is described herein with reference to the preferred embodiment, one skilled in the art will readily appreciate that other applications may be substituted for those set forth herein without departing from the spirit and scope of the invention. For example, the invention is described when applied in conjunction with a particular pulse generator and programming system. Thus, the displays herein, as well as information stored and reported, are a function of the capability of the exemplary cardiac therapy system described in the specification. It should be appreciated that other implantable medical devices, such as cardiac therapy devices, may be used in conjunction with the invention. Accordingly, the invention should only be limited by the Claims included below.

I claim:

1. Apparatus for presenting patient electrocardiogram and implantable device status information, comprising:

an implanted cardiac therapy device including means for sensing a patient electrocardiogram signal and a processor for generating and collating device status information, said status information including cardiac event interval information, why a therapy was or was not applied, and patient response to therapy, and for storing said status information and said patient electrocardiogram signal;

output means in said implanted cardiac therapy device having an input for receiving said stored electrocardiogram signal and status information and for assembling and outputting a data frame therefrom;

an external display apparatus including a decoder for separating said data frame into said electrocardiogram signal and said status information; and a display for presenting said electrocardiogram signal and said status information with portions of said status information presented in said display in proximity to portions of said electrocardiogram signal to which they relate.

2. The apparatus of claim 1 wherein said sensed patient electrocardiogram signal comprises an analog signal and said stored electrocardiogram signal comprises a digital signal, said apparatus further comprising:

an analog to digital converter for receiving said analog patient electrocardiogram from said means for sensing and for converting said analog electrocardiogram signal into a digital electrocardiogram signal.

3. The apparatus of claim 2, wherein said output means comprises a multiplexer.

4. The apparatus of claim 1, further comprising a means for storing said data frame.

5. The apparatus of claim 1, wherein said output means includes telemetry means for transmitting said data frame from said implanted cardiac therapy device to said external display apparatus.

6. The apparatus of claim 1, wherein said output means includes means for multiplexing the portion of said data frame including said device status information into a portion of said stored electrocardiogram signal corresponding to a refractory period of said electrocardiogram signal.

7. A method for presenting status information included with an electrocardiogram, comprising the steps of:

generating in an implanted therapy device a data frame by multiplexing in said data frame patient electrocardiogram information and device status information, said status information including cardiac event interval information and why a therapy was or was not applied;

providing said data frame to an external instrument having a display apparatus;

demultiplexing said data frame to separate said data frame into said electrocardiogram information and said status information; and presenting the separated status information and patient electrocardiogram information on said display apparatus in a correlated manner whereby status information from a particular point in time is presented proximate the portion of the electrocardiogram to which it relates.

8. The method of claim 7, wherein said step of generating a data frame includes interleaving said status information in a portion of said electrocardiogram information corresponding to a refractory period of said electrocardiogram information.

9. The method of claim 7, further comprising the step of storing said data frame.

10. A cardiac diagnostic method, comprising the steps of:

providing an implanted cardiac therapy device;

acquiring a patient electrocardiogram with said device;

generating device status information including cardiac event interval information, why a therapy was or was not applied, and patient response to therapy;

collating said patient electrocardiogram and said implanted cardiac therapy device status information:

providing a data frame;

assembling said collated information into said data frame; and storing said data frame for later retrieval.

11. The method of claim 10, further comprising the steps of:

disassembling said data frame into electrocardiogram information and status information; and presenting the information derived from said data frame.

12. The method of claim 10, said collating step further comprising interleaving said electrocardiogram information with said status information within each data frame.

13. A method for presenting information included with an electrocardiogram, comprising the steps of:

collecting patient ECG and implantable cardiac therapy device status information, including cardiac event interval information, why therapy was or was not applied, and patient response to therapy;

generating a data frame;

correlating said ECG and status information in said data frame;

storing said data frame in a memory of an implanted cardiac therapy device;

transmitting via telemetry said data frame from said memory to an external instrument; and separating said ECG from said status information and presenting said ECG and status information on a display.

14. Apparatus for presenting patient electrocardiogram and implantable device status information comprising:

means for collecting patient ECG and cardiac apparatus status information, including cardiac event interval information, why therapy was or was not applied, and patient response to therapy, relating to a detected arrhythmic episode;

means for correlating said information in a data frame with said ECG for storage;

telemetry means; and means for receiving and displaying said patient ECG and cardiac apparatus status information.

15. An external instrument for a cardiac therapy system, comprising:

means for separating a data frame received from an implanted cardiac therapy device into patient ECG and cardiac apparatus status information, said status information including cardiac event interval information, why therapy was or was not applied, and patient response to therapy, relating to a detected arrhythmic episode information; and means for presenting said patient ECG and cardiac apparatus status information.

* * * * *